US00PP17916P2

(12) United States Plant Patent
Schouten

(10) Patent No.: US PP17,916 P2
(45) Date of Patent: Aug. 14, 2007

(54) *AESCHYNANTHUS* PLANT NAMED 'TWISTER'

(50) Latin Name: *Aeschynanthus hybrida*
Varietal Denomination: Twister

(75) Inventor: Albert Schouten, Sleeuwijk (NL)

(73) Assignee: New Variety B.V., Aalsmeer (NL)

( * ) Notice: Subject to any disclaimer, the term of this patent is extended or adjusted under 35 U.S.C. 154(b) by 0 days.

(21) Appl. No.: 11/323,168

(22) Filed: Dec. 30, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

GTITM UPOVROM Citation for 'Twister' as per QZ PBR 20041082; Jun. 15, 2004.*

* cited by examiner

*Primary Examiner*—Kent Bell
(74) *Attorney, Agent, or Firm*—C. A. Whealy

(57) ABSTRACT

A new and distinct cultivar of *Aeschynanthus* plant named 'Twister', characterized by its cascading and pendulous plant habit; small leaves that are reflexed and concave; dark green-colored upper leaf surfaces and lighter green-colored lower leaf surfaces; and large bright red-colored flowers.

2 Drawing Sheets

Botanical designation: *Aeschynanthus hybrida.*
Cultivar denomination: 'Twister'.

BACKGROUND OF THE INVENTION

The present Invention relates to a new and distinct cultivar of *Aeschynanthus* plant, botanically known as *Aeschynanthus hybrida,* and hereinafter referred to by the cultivar name Twister.

The new *Aeschynanthus* is a naturally-occurring branch mutation of the *Aeschynanthus hybrida* cultivar Rasta, not patented. The new *Aeschynanthus* was discovered and selected from within a population of plants of the cultivar Rasta in a controlled environment in Sleeuwijk, The Netherlands in May, 2003.

Asexual reproduction of the new cultivar by cuttings since August, 2003 in Sleeuwijk, The Netherlands has shown that the unique features of this new *Aeschynanthus* are stable and reproduced true to type in successive generations.

SUMMARY OF THE INVENTION

Plants of the cultivar Twister have not been observed under all possible environmental conditions. The phenotype may vary somewhat with variations in environment such as temperature and light intensity without, however, any variance in genotype.

The following traits have been repeatedly observed and are determined to be the unique characteristics of 'Twister'. These characteristics in combination distinguish 'Twister' as a new and distinct cultivar:

1. Cascading and pendulous plant habit.
2. Small leaves that are reflexed and concave.
3. Dark green-colored upper leaf surfaces and lighter green-colored lower leaf surfaces.
4. Large bright red-colored flowers.

Plants of the new *Aeschynanthus* differ primarily from plants of the parent, the cultivar Rasta, in the following characteristics:

1. Plants of the new *Aeschynanthus* are more compact than plants of the cultivar Rasta.
2. Plants of the new *Aeschynanthus* have darker green-colored foliage than plants of the cultivar Rasta.
3. Leaves of plants of the new *Aeschynanthus* are reflexed and concave whereas leaves of plants of the cultivar Rasta are reflexed and flat.

Plants of the new *Aeschynanthus* differ from plants of unnamed selections of *Aeschynanthus* known to the Inventor in the following characteristics:

1. Plants of the new *Aeschynanthus* have smaller leaves than plants of unnamed selections of *Aeschynanthus* known to the Inventor.
2. Plants of the new *Aeschynanthus* have reflexed and concave leaves whereas plants of unnamed selections of *Aeschynanthus* known to the Inventor have non-curled and flat leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Aeschynanthus.*

The photograph on the first sheet comprises a side perspective view of a typical plant of 'Twister' grown in a container.

The photograph at the top of the second sheet is a close-up view of typical flowers of 'Twister'.

The photograph at the bottom of the second sheet is a close-up view of typical leaves and lateral branch of 'Twister'.

DETAILED BOTANICAL DESCRIPTION

Plants of the cultivar Twister have not been observed under all possible environmental conditions. The phenotype may vary somewhat with variations in environment such as temperature and light intensity, without, however, any variance in genotype. The aforementioned photographs and following observations and measurements describe plants grown during the winter in Sleeuwijk, The Netherlands, under commercial practice in a glass-covered greenhouse with day temperatures ranging from 18° C. to 25° C. and night temperatures ranging from 15° C. to 18° C. Plants used for the photographs and description were about 1.5 years old. In the following description, color references are made to The Royal Horticultural Society Colour Chart, 2001 Edition, except where general terms of ordinary dictionary significance are used.

Botanical classification: *Aeschynanthus hybrida* cultivar Twister.

Parentage: Naturally-occurring branch mutation of the *Aeschynanthus hybrida* cultivar Rasta, not patented.

Propagation:

*Method.*—By cuttings.

*Time to initiate roots.*—About two weeks at 20° C.

*Time to produce a rooted young plant.*—About 40 days at 20° C.

*Root description.*—Fine, fibrous; brown in color.

*Rooting habit.*—Freely branching; dense.

Plant description:

*Form.*—Perennial flowering plant; cascading and pendulous plant habit. Freely basal branching habit; about 20 lateral branches per plant; pinching enhances branching.

*Plant height.*—About 12 cm.

*Plant length* (*top of plant plane to apices of lateral branches*).—About 51 cm.

*Plant diameter.*—About 64 cm.

*Vigor.*—Vigorous.

*Lateral branches.*—Length: About 44 cm. Diameter: About 2.5 mm. Internode length: About 1.4 cm. Texture: Densely tomentose. Color: 139A tinted with close to 187A; at the nodes, 137B.

*Foliage description.*—Arrangement: Opposite, simple. Length: About 2.3 cm. Width: About 8 mm. Shape: Narrowly lanceolate. Apex: Acute. Base: Obtuse to truncate. Margin: Entire. Aspect: Reflexed and concave. Texture, upper surface: Smooth, glabrous; margins, pubescent. Texture, lower surface: Pubescent. Venation pattern: Pinnate. Color: Developing leaves, upper surface: 138A to 138B. Developing leaves, lower surface: 138C to 139D. Fully expanded leaves, upper surface: Darker than 136A; venation, darker than 136A. Fully expanded leaves, lower surface: 146A; venation, 136A to 137A. Petiole length: About 2 mm. Petiole diameter: About 1 mm. Petiole texture, upper and lower surfaces: Pubescent. Petiole color, upper and lower surfaces: 146B to 146C tinted with close to 187A.

Flower description:

*Flower type and habit.*—Single tubular flowers solitary or in pairs; terminal or axillary. Freely flowering habit, usually about 64 flowers and flower buds per plant. Flowers not persistent. Flowers not fragrant. Flowers face mostly outward.

*Natural flowering season.*—Flowering continuous during the spring in The Netherlands.

*Flower longevity.*—Flowers last about five days on the plant.

*Flower diameter.*—About 3 cm.

*Flower depth.*—About 7.4 cm.

*Flower buds.*—Length: About 2.8 cm. Diameter: About 9 mm. Shape: Elongated oblong. Color: 187A.

*Corolla.*—Shape/arrangement: Tubular; five fused petals. Petal apices: Obtuse. Petal margin: Entire. Petal length: About 7.4 cm. Petal width: About 1.1 cm. Texture, upper and lower surfaces of petal lobes: Pubescent. Color: When opening, inner surface: Tube, 22C; towards the base, 37B to 37C; towards the apex, 45A to 45B. When opening, outer surface: 45B to 46B. Fully opened, inner surface: Tube, 22C; towards the base, 37B to 37C; towards the apex, 45B to 46B. Fully opened, outer surface: 45A.

*Calyx.*—Length: About 3 cm. Diameter: About 1.1 cm. Shape: Tubular. Sepal apex: Obtuse. Sepal margin: Entire. Number: Calyx is five parted. Sepal texture, upper and lower surfaces: Pubescent. Color, inner surface: Slightly lighter than 187A. Color, outer surface: 187A.

*Peduncles.*—Length: About 1.5 cm. Diameter: About 1.5 mm. Strength: Moderately strong to strong. Angle: About 30° from the stem. Color: 146A.

*Reproductive organs.*—Androecium: Stamen quantity: Four per flower in pairs. Filament length: About 2.5 cm. Filament color: 145C; towards the apex, 39A. Anther length: About 3 mm. Anther shape: Ovate. Anther color: 197B. Pollen amount: Moderate. Pollen color: 198A. Gynoecium: Pistil quantity: One per flower. Pistil length: About 7 cm. Style length: About 6.9 cm. Style color: 150B to 150C. Stigma shape: Two-parted. Stigma color: 150D. Ovary color: 151C.

*Seed/fruit.*—Seed and fruit development has not been observed.

Disease/pest resistance: Plants of the new *Aeschynanthus* have not been observed to be resistant to pathogens and pests common to *Aeschynanthus*.

Temperature tolerance: Plants of the new *Aeschynanthus* have been observed to tolerate temperatures from about 10° C. to 40° C.

It is claimed:

1. A new and distinct cultivar of *Aeschynanthus* plant named 'Twister', as illustrated and described.

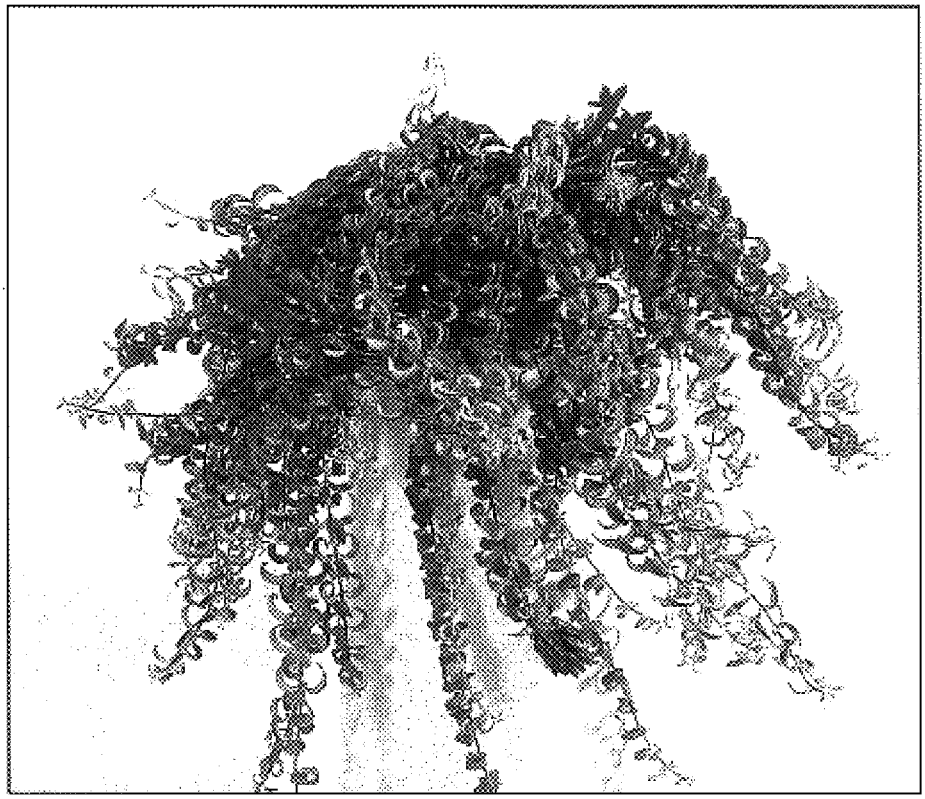

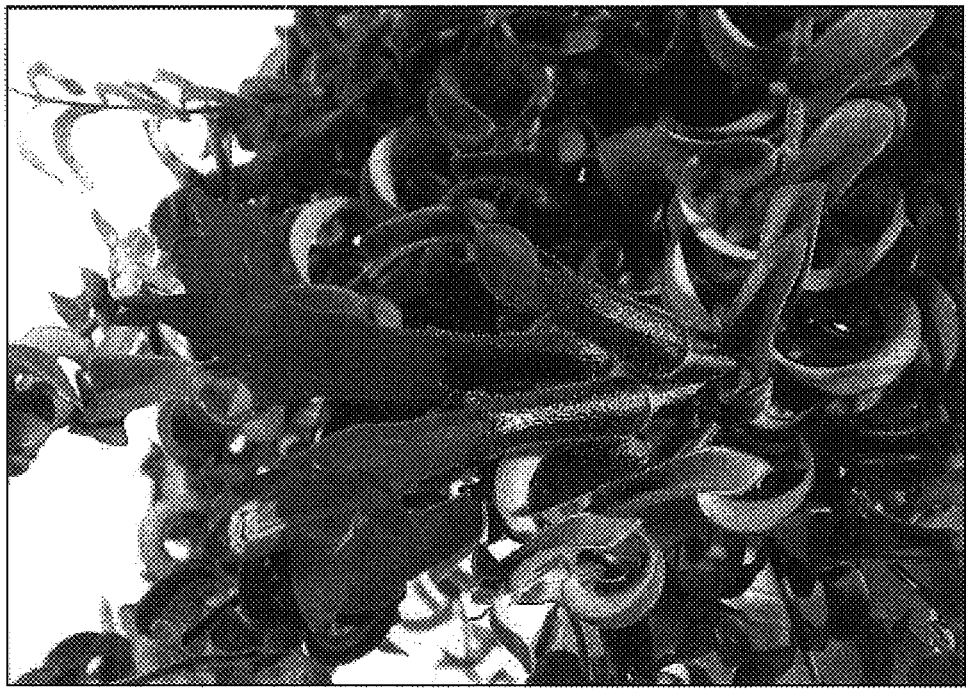
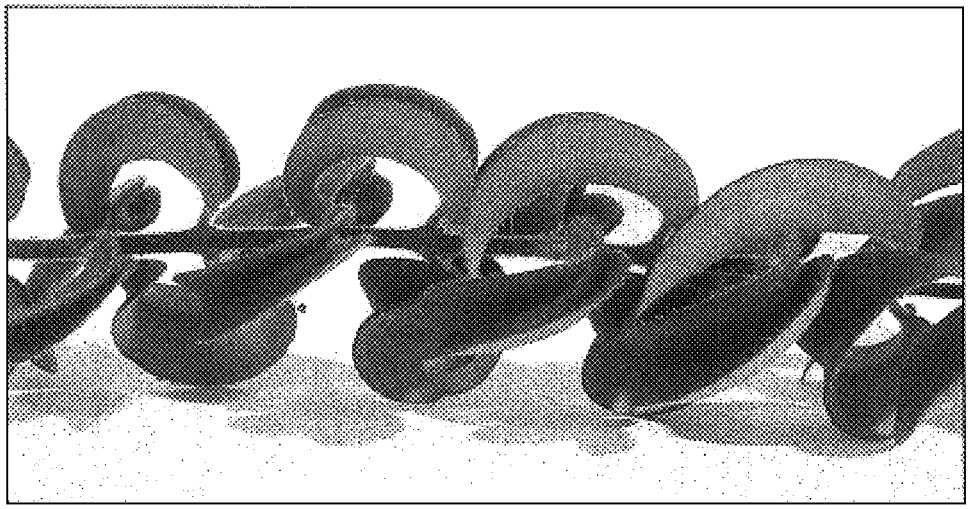

* * * * *